United States Patent [19]

Fischer

[11] Patent Number: Plant 5,923

[45] Date of Patent: Mar. 31, 1987

[54] AFRICAN VIOLET PLANT NAMED OLYMPIA

[75] Inventor: Arnold Fischer, Hanover, Fed. Rep. of Germany

[73] Assignee: Ball Pan Am Plant Company, Parrish, Fla.

[21] Appl. No.: 632,107

[22] Filed: Jul. 18, 1984

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of African violet named Olympia, particularly characterized by its distinctive pink-lavender flowers, its excellent year round performance with good heat tolerance, profuse flowering, and by its medium green, pubescent foliage.

2 Drawing Figures

1

The present invention comprises a new and distinct cultivar of African violet plant, botanically known as *Saintpaulia ionantha*, and hereinafter referred to by the cultivar name Olympia.

The new cultivar was referred to during the breeding and selection process by the designated V7-H37-N, and is a product of a planned breeding program. The basic objective of the breeding program was to create a new African violet cultivar having a distinctive pink-lavender color, early flowering, and floriferous habit.

The new cultivar was originated from a cross made in a controlled breeding program in Hannover, Germany. The male and female parents are unknown at this time.

Olympia was discovered and selected by me as a flowering plant within the progeny of the stated cross in a controlled environment in Fallbrook, Calif. Asexual reproduction of the new cultivar by leaf cuttings, as performed by me at West Chicago, Ill. and Parrish, Fla. has demonstrated that the combination of characteristics as herein disclosed for the new cultivar are firmly fixed and retained through successive generations of asexual reproduction.

Olympia has not been observed under all possible environmental conditions. The phenotype may vary significantly with variations in environment such as temperature, light intensity and day length. The following observations, measurements and values describe the new cultivar as grown in Parrish, Fla. under greenhouse conditions which closely approximate those generally used in commercial practice.

The following traits have been repeatedly observed and are determined to be basic characteristics of Olympia which in combination distinguish this African violet as a new and distinct cultivar:

(1) Distinctive pink-lavender flowers.

(2) Excellent year round performance with good heat tolerance.

(3) Suitable for production in 10 cm. pots for flowering in 9–12 weeks depending upon growing conditions.

(4) Very floriferous, with flowers continuing to develop for weeks after onset of flowering; large bouquet is carried above dark green foliage.

(5) Medium green, pubescent foliage with a crenate leaf margin.

The new cultivar is most similar to Marta, disclosed in U.S. Plant Pat. No. 3,610. Olympia is principally

2 distinguished from Marta by its distinctive pink-lavender flowers.

The accompanying photographic drawings show a typical specimen plant of the new cultivar.

Sheet 1 is a color photograph in perspective view.

Sheet 2 is a black and white photo in which, one flower is illustrated with true color value. The colors appearing in the photographs are as true as possible with color illustrations of this type.

In the following description, color references are made to The Royal Horticultural Society Colour Chart (RHS), except where general colors of ordinary significance are referred to. Color values were taken under 5000 foot candles of natural light at approximately 11:30 A.M. in Parrish, Fla.

Botanical classification: *Saintpaulia ionantha*, Ramat. cv. Olympia.

Parentage:

*Male parent.*—Unknown.

*Female parent.*—Unknown.

Propagation: The new cultivar holds its distinguishing characteristics through successive propagations by leaf cuttings.

Plant: From 4 cm. to 6 cm. tall when grown in pots, and approximately 24 cm. in diameter when fully grown. The growth rate is vigorous, and the general shape of the full grown plant is round.

*Leaves.*—Quantity: abundant. Shape: cordate with crenate margins. Diameter: 2 to 2¾ cm. Texture: pubescent, glossy. Ribs and Veins: pinnate. Color (upperside): 147A. Color (underside): 47D on outermost edge; veins 147C, and middle surrounding veins 186C. Peticles: 2–8 cm. in length.

*Flowers.*—Buds: Size: ½ to 1 cm. in diameter. Shape: round. Rate of opening: normal. Color: 73D to 74D. Sepals: Shape: lanceolate. Color: 184B with a hint of 138D. Phyllaries: 2, lanceolate. Color (upperside): 147A. Color (underside): 184A. Calyx: Shape: funnel. Size: 10–12 mm. in diameter.

*Peduncle.*—Length: 3–7 cm. Character: rigid, erect. Color: 183A with a tint of 147D.

*Individual flowers.*—Number of petals: 5 Shape: cup shaped when bloom first opens, becoming slightly flat when mature. Color: Upperside: 78C; 78D or slightly lighter on margin of petals. Underside: 73C fading to 73D. Flowers fade slightly as they age. Borne: cymosa clusters form on peduncles 3 to 7 cm. long. Flowering habit: Flowers profusely and intermittently year round with blooms lasting 2–3 weeks after which petals dry up but do not drop. A 2½" plantlet placed in a 10 cm. pot finishes in 9–11 weeks.

*Reproductive organs.*—Stamens: 2, borne singly on one side of the ovary. Anthers basifixed. Anthers: 2 mm.×2 mm., yellow. Filaments: 2–3 mm., violet-yellow. Pollen Color: yellow. Pistels: Number: 1 5–7 mm. long. Styles: 1. Stigma: sticky, white. Ovaries: superior.

*Roots.*—Fiberous and fine.

*Disease resistance.*—No African violet diseases observed to date.

*General observations.*—Olympia is characterized by its bouquet of large pink-lavender flowers, held above dark green foliage, and by its profuse and early flowering.

I claim:

1. A new and distinct cultivar of African violet named Olympia, as illustrated and described, and particularly characterized by its distinctive pink-lavender flowers, its excellent year round performance with good heat tolerance, profuse flowering, and by its medium green, pubescent foliage.

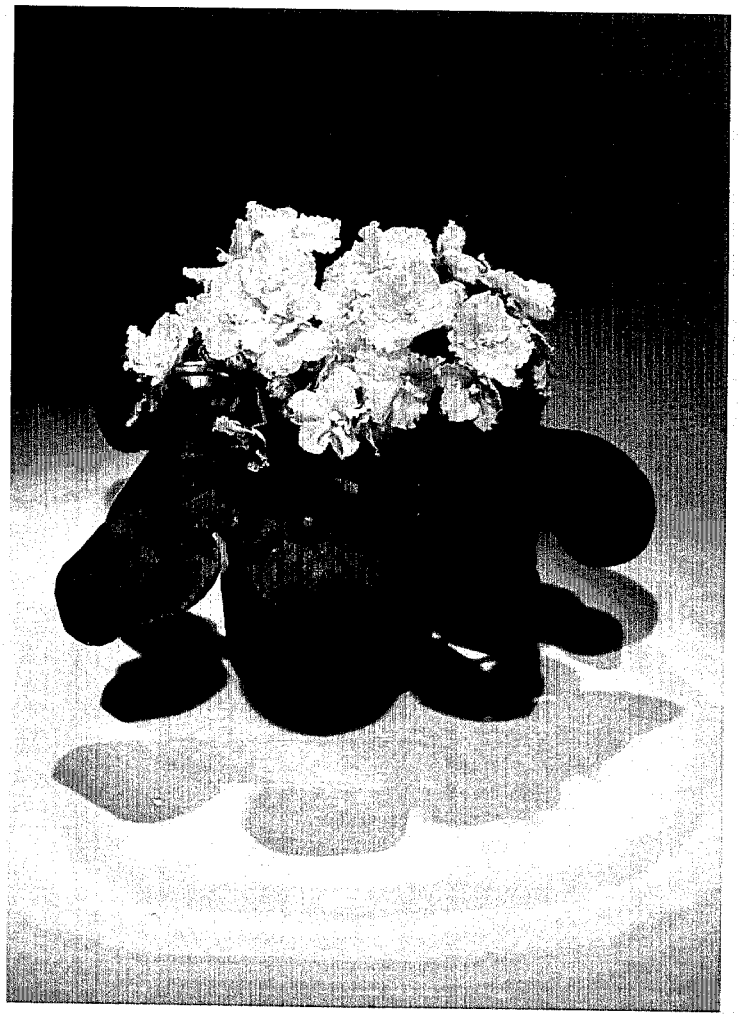

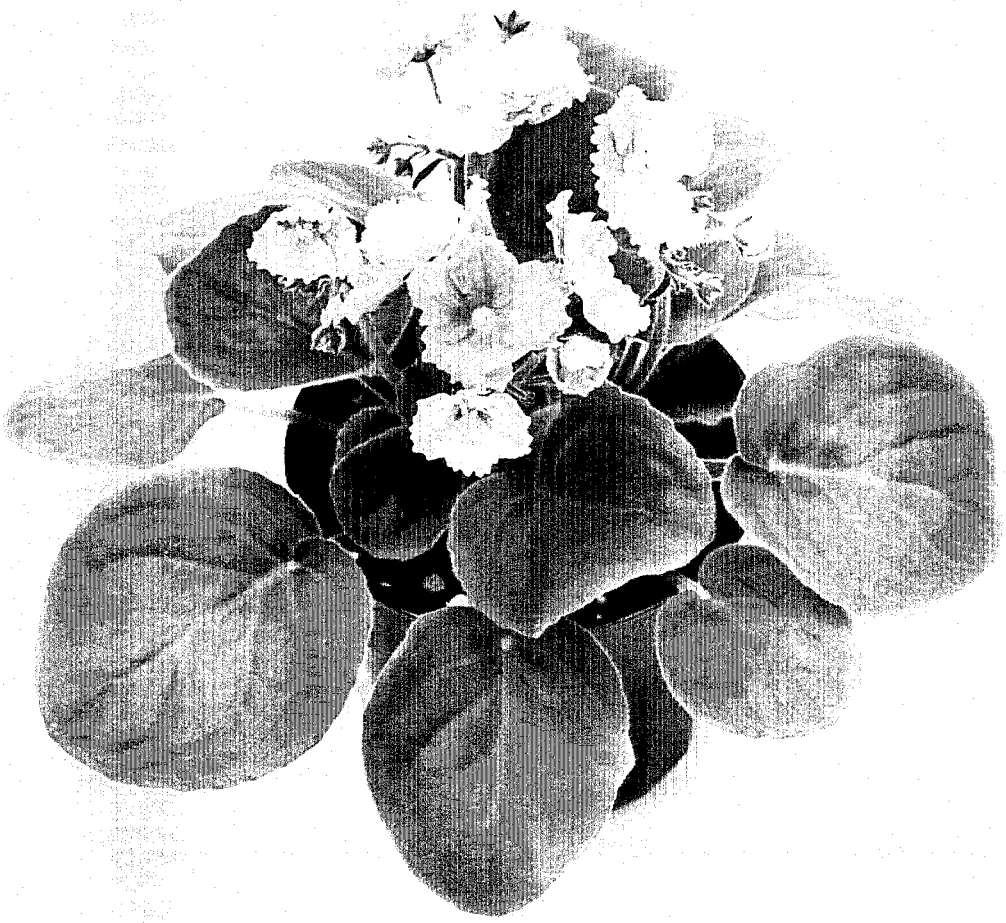

* * * * *